United States Patent [19]

Oka et al.

[11] Patent Number: 5,015,094

[45] Date of Patent: May 14, 1991

[54] PARTICLE SIZE MEASURING SYSTEM

[75] Inventors: Koichi Oka, Otsu; Akira Kawaguchi, Kyoto; Kunio Kumagai, Koga; Katsuhiro Morisawa, Hirakata, all of Japan

[73] Assignee: Otsuka Electronics Co., Ltd., Osaka, Japan

[21] Appl. No.: 413,647

[22] Filed: Sep. 28, 1989

[30] Foreign Application Priority Data

Oct. 3, 1988 [JP] Japan ............................... 63-249336

[51] Int. Cl.$^5$ ............................................ G01N 15/02
[52] U.S. Cl. ................................... 356/336; 356/335; 356/337
[58] Field of Search ............................... 356/335–343, 356/246; 250/584, 574, 576

[56] References Cited

U.S. PATENT DOCUMENTS 4,830,494 5/1989 Ishikawa et al. ...................... 356/336

FOREIGN PATENT DOCUMENTS 63-265138 11/1988 Japan .
63-265139 11/1988 Japan .

Primary Examiner—Davis L. Willis
Assistant Examiner—Hoa Pham
Attorney, Agent, or Firm—Sughrue, Mion, Zinn, Macpeak & Seas

[57] ABSTRACT

There is disclosed a system in which, according to the time domain method, a laser light is irradiated to an object to be measured, photon pulses based on the scattering light from the object to be measured are received, time series data are generated based on the light receiving signal, and based on the time series data thus generated, the particle size distribution of particles in the object to be meansed is measured. Thus, the present invention achieves a considerable reduction in time required for finally obtaining the particle size based on the measured data, as compared with a conventional system using a calculator program.

3 Claims, 5 Drawing Sheets

PARTICLE SIZE MEASURING SYSTEM

BACKGROUND OF THE INVENTION

The present invention relates to a particle size measuring system, and more particularly to a particle size measuring system arranged based on a so-called dynamic light scattering method, in which a laser light is irradiated to an object to be measured, photon pulses based on a scattering light therefrom are received, time series data are generated from a light receiving signal, and based on the time series data thus generated, the particle size distribution of particles in the object to be measured is measured.

It is known that particles exhibit a Brownian movement in a liquid or gas, and when a laser light is irradiated on the particles, there occurs a Rayleigh scattering. According to a Homodyne method, photon pulses generated based on the scattering light at a predetermined scattering angle, may be received in the form of time series data, of which self correlation function (in term of an exponential function) may be obtained. It is known that the particle diffusion constant may be obtained from this self correlation function and the particle size is obtained from this diffusion constant. However, the particles do not always have the same particle size. Accordingly, the correlation function obtained is of the function type in which a number of exponential functions are composed. However, according to a predetermined approximation method, the particle size distribution may be obtained from an experimentally obtained correlation function form.

There are known two different methods of obtaining the correlation function from the received time series data, i.e., a hardware method of executing a photon correlation operation with the use of a shift register, and a software method of executing a photon correlation operation with the use of a computer.

According to the software method, the precision of the photon correlation operation may be set with relatively high degree of freedom according to the software applied. Accordingly, the software method is being widely used.

The following description will discuss in more detail the software method.

A laser light is irradiated to an object to be measured, from which a scattering light is generated. The scattering light thus generated is received to generate time series data. The time series data thus generated are once stored means in a storage. Based on the time series data thus stored, necessary operations are executed to calculate the particle size distribution of particles in the object to be measured. That is, based on the time series data, predetermined correlation operations are executed by a computer to calculate the particle size of the particles contained in the object to be measured.

More specifically, to calculate the particle size, it is required to generate time series data of photon pulses which represent variations of the photon pulse density with the passage of time. To generate the time series data, a time domain method and a time interval method are generally adopted.

According to the time domain method as shown in FIG. 5 (A), the number of photon pulses per one interval of reference clock pulses is measured by a counter, and the counted data of the respective intervals are formed as a chain of time series data. Based on the time series data, predetermined correlation operations are executed to calculate the particle size distribution of the particles contained in an object to be measured.

Accordingly, this method is advantageous for an application where the number of photon pulses is relatively great. The condition that the number of photon pulses is relatively great, is satisfied when the particle size is relatively great and the scattering light intensity is considerably high. Thus, the time domain method may be regarded as a method which achieves a particle size measurement with high precision where the particle size is relatively great and the scattering light intensity is considerably high.

According to the time interval method as shown in FIG. 5 (B), the number of reference clock pulses appearing in one time interval in a photon pulse train, and the counted data are formed as a chain of time series data. Accordingly, this method is effective even though the number of photon pulses is relatively small, as far as the clock rate is properly set. That is, the time interval method achieves a particle size measurement with high precision where the particle size is relatively small and the scattering light intensity is considerably low.

Generally, a particle size measuring system employs either one of the methods above-mentioned. These methods respectively determine optimum particle size measuring ranges. Accordingly, there is proposed a particle size measuring system in which both methods are combined to achieve an accurate particle size measurement in a wide range (Refer to JP-Patent laid open publications No. 265138/1988 published on Nov. 1, 1988 and No. 265139/1988 published on Nov. 1, 1988, both filed by the Applicant).

The particle size measuring system using the time domain method, the time interval method or both methods combined, presents the following problems in executing the operations.

According to the time domain method, the correlation function $g_2(\tau)$ based on photon pulses is obtained in the following manner.

Since $\tau$ is handled in a discrete manner, $\tau$ is expressed in term of a multiplication $i\Delta t$ by a clock pulse interval $\Delta t$ (i=1, ...., M), in which i represents a channel.

$$g_2(\tau) = g_2(i\Delta t) = N^2 \sum_{j=1}^{N-i} (n_{TDj} \times n_{TDj+i})/(N-i) \left( \sum_{j=1}^{N} n_{TDj} \right)^2$$

where $n_{TDj}$ is the jth data representing the number of photon pulses, the channel i is a natural number from 1 to M, M is the number of channels representing the maximum value of i, and N is the total number of obtained data.

To execute the operation expressed by the equation above-mentioned, it is required that i is set to numerals from 1 to M, and $\Sigma$ is obtained for a range from j=1 to j=N−i for each i. Accordingly, the number of calculations approximately amounts to (M×N).

For example, there is now supposed a 16k-word RAM as a memory for storing data representing the number of photon pulses. In this case, the number of data N amounts to 16,384. When the number of channel is 64, the total number of calculations is about 1,048,576. If one operation takes about 5 μsec in a personal computer, all operations take about 5 seconds. When considering the time required for taking out data from the RAM and storing data in the RAM before and after each of the operations, the total time required is further lengthened. This is apparent from the fact that, when the maximum number of accesses is about ($3 \times 10^7$) and one access takes 200 nsec., a period of time of about 6 seconds is required. Accordingly, it is considered that one processing of measured data takes a considerable period of time. In general, since only one measurement assures no precision, a number of measurements are made so that the integrated average is calculated. Accordingly, the processing may extend over one hour, until reliable data are obtained.

Accordingly, since the measuring period of time and the processing period of time are limited even though it is desired to carry out a number of measurements to improve the precision, the number of measurements is limited, resulting in aquirement of less precise data. Further, there are instances where the temperature of an object to be measured undergo a change during measurement (for example, when the measurement is made with an electric field applied, the temperature of the object to be measured may be increased due to a Joule heat with the passage of time). In this case, with the passage of time, the measured data vary, resulting in occurrence of measurement errors. Further, there are instances where, due to settling of particles in the object to be measured, the received light intensity is gradually decreased to make it difficult to further continue the measurement. Moreover, if an unexpected disturbance is externally entered, the reliability of measured data is decreased.

Of course, a mini-computer, a medium-size or large-size computer may be used to shorten the operating period of time. However, this disadvantageously makes the entire system large-sized, resulting in considerable increase in cost.

Also, the time interval method presents a problem in view of operation time.

More specifically, when data representing the number of clock pulses are $n_{TIj}$, integration of $$\sum_{j=s}^{p} n_{TIj}$$

for $s=1$ is made for each of $p=s, s+1, s+2$ and so forth until $$\sum_{j=s}^{p} n_{TIj}$$

reaches the maximum number of channels M or until p reaches N. The similar operations are repeated for each of $s=2, 3, \ldots, N$. Then, the number of $$\sum_{j=s}^{p} n_{TIj}$$

where $$\sum_{j=s}^{p} n_{TIj}$$

is equal to i, is regarded as the correlation data T(i) of the channel i. By normalization, there may be obtained the correlation function $g_2(\tau)$ as shown by the following equation:

$$g_2(\tau) = g_2(i\Delta t) = T(i) / \left( N / \sum_{j=1}^{N} n_{TIj} \right)^2 \left( \sum_{j=1}^{N} n_{TIj} - i \right)$$

As apparent from the foregoing, to obtain the correlation data T(i) requires one to calculate Σ for a range from j=s to j=p for each of s=1, 2, 3, ..., N. When it is supposed that $n_{TIj}$ is equal to 1 for all j, this means that Σ is calculated until $$\sum_{j=s}^{p} n_{TIj}$$

always reaches M. Accordingly, the number of operations amounts to about (M×N). This is the same as in the time domain method. The number of clock pulses per photon pulse is not always equal to 1. It is therefore known that the number of operations is decreased in inverse proportion to the number of clock pulses for each photon pulse. However, since the number of clock pulses for one photon pulse is about five or six, the number of operations is extremely great, requiring a long calculating period of time.

SUMMARY OF THE INVENTION

It is an object of the present invention to provide a particle size measuring system in which the data operation processing time is shortened to increase the number of particle size measurements within a limited measuring period of time, thereby to improve the measurement precision.

To achieve the object above-mentioned, the particle size measuring system in accordance with the present invention, as applied to the time domain method, features:

time series data generating circuitry for generating time series data representing the number of photon pulses per unit time;

first and second memories for storing the time series data;

reading circuitry for successively reading, from the memories, time series data separated by a predetermined period of time from one another; and multiplication & accumulation operation circuitry for multiplying the read time series data by one another and for accumulating the multiplication results, the multiplication and accumulation being executed simultaneously with the reading operation by the reading means.

According to the system having the arrangement above-mentioned, the operations may be executed and finished within a short period of time. That is, there may be simultaneously carried out (i) an operation for successively reading, from the memories, time series data separated by a predetermined period of time from one another, and (ii) an operation for multiplying the read time series data and for accumulating the multiplication results, the respective operations having conventionally taken a major part of the entire processing time.

The particle size measuring system in accordance with the present invention, as applied to the time interval method, features:

time series data generating circuitry for generating time series data representing a photon pulse time interval;

a memory for accumulating the time series data;

reading circuitry for successively reading the time series data from the memory;

accumulation operation circuitry for accumulating, simultaneously with the reading operation by the reading means, the read time series data over a predetermined range;

a memory for successively storing the accumulation results; and counting circuitry for reading from time to time, simultaneously with the accumulation operation by the accumulation operation circuitry, the accumulation result data from the last-mentioned memory, thereby to obtain correlation data based on the number of accumulation result data thus read.

According to the system having the arrangement above-mentioned, the operating period of time may be shortened. That is, there may be simultaneously carried out (i) an operation for successively reading time series data from the memory, (ii) an operation for accumulating the read time series data over a predetermined range, and (iii) an operation for obtaining the correlation data, the respective operations having conventionally taken a major part of the entire processing time.

The present invention may be embodied as a particle size measuring system which may be applied both to the time domain method and the time interval method, according to the scattering light intensity, and which comprises selection means for selecting the time series data generating means used for the time domain method, or the time series data generating means used for the time interval method.

The apparatus above-mentioned may select, according to the scattering light intensity, either the time domain method or the time interval method so that optimum particle size operations and processings may be executed.

According to the particle size measuring system of the present invention applied to the time domain method or the time interval method, both the measured data reading operation and the arithmetic processing operation may be simultaneously carried out. This achieves a considerable reduction in processing time required for finally obtaining the particle size based on the measured data.

Further, when the present invention is applied to a particle size measuring system of the type in which the time domain method or the time interval method is automatically selected according to the scattering light intensity, measurement of particle size may be achieved over a wide particle-size range with high precision. In addition, time reduction may also be achieved in the same manner as above-mentioned.

Accordingly, the number of particle size measurements may be increased in a limited measuring period of time, thereby to improve the precision of obtained particle size data. Further, since a period of time required for one measurement is shortened, the measurement is less affected by variations of the ambient temperature, and less influenced by noise, external disturbance and the like. Also, the measurement is less affected by variations of a sample to be measured with the passage of time or variations of the ambient conditions. Further, since a period of time required for one measurement is shortened, it is possible to measure variations of the particle size due to variations of the sample conditions and the like.

The features of the present invention will be apparent from the following description with reference to the attached drawings.

DETAILED DESCRIPTION OF THE PREFERRED EMBODIMENTS

The following description will discuss in detail the present invention with reference to the attached drawings showing an embodiment thereof.

Figure 3:
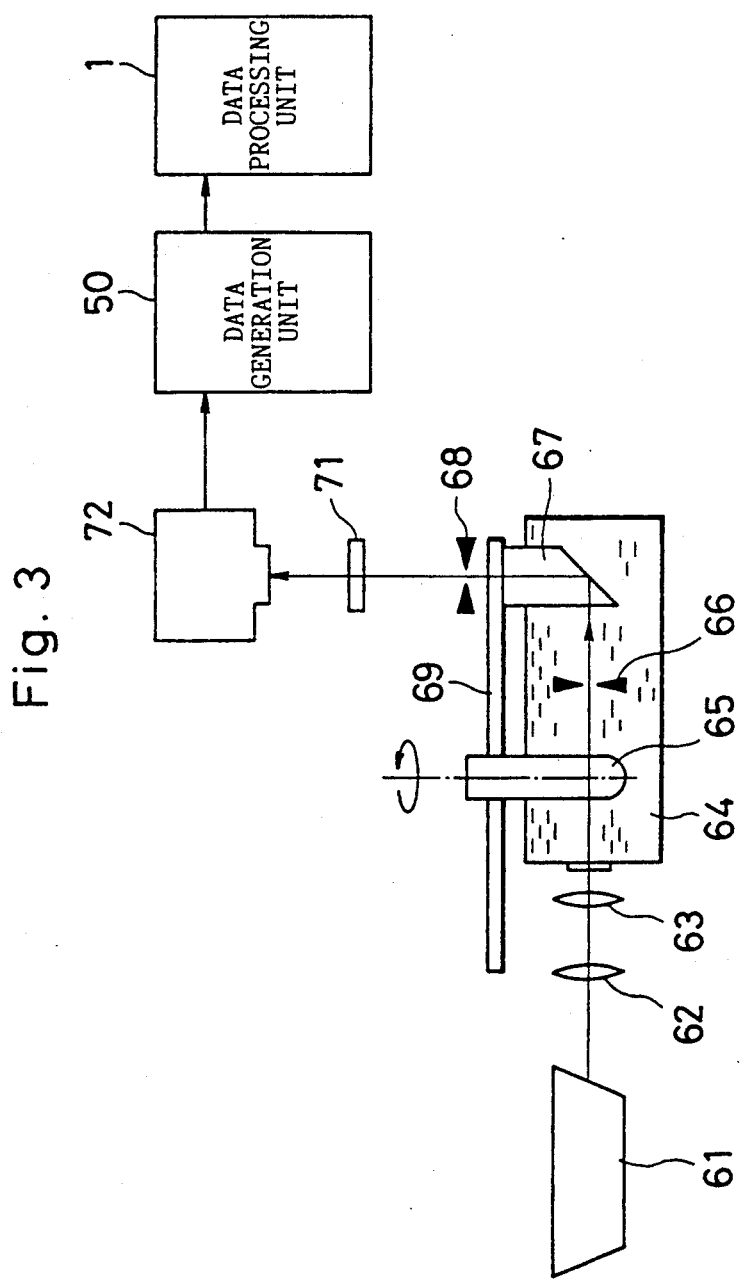
FIG. 3 is a general schematic block diagram of a particle size measuring system.

FIG. 3 is a schematic block diagram of an example of an optical measuring system and the like in a particle size measuring system.

Light from a laser device 61 is guided, through collimator lenses 62, 63, to a cell 65 disposed in a thermostat reservoir 64. The cell 65 is charged with a solution to be measured. The light scattered, at a predetermined angle, by particles in the solution to be measured, passes through a pinhole 66 and is reflected by a prism 67. The prism 67 is attached to a goniometer 69 rotatable around the center axis of the cell 65. This allows the taking of data at an arbitrary scattering angle. The light reflected by the prism 67 passes through a pinhole 68 and a filter 71, and is sent to a photomultiplier 72 serving as a light receiver. The pinholes 66, 68 are formed at such positions that coherence conditions are satisfied.

It is understood that the optical measuring system is not limited to that described above. For example, the thermostat reservoir 64, the prism 67, the angle variable function, the filter 71 and the like are not always indispensably required.

An output signal from the photomultiplier 72 is entered into a data generation unit 50, which executes a predetermined processing on this signal. The signal is then taken out as a time series photon pulse signal or a time series clock pulse signal. The time series pulse signal thus taken, is entered into a data processing unit 1, which executes arithmetic and data processing.

Figure 2:
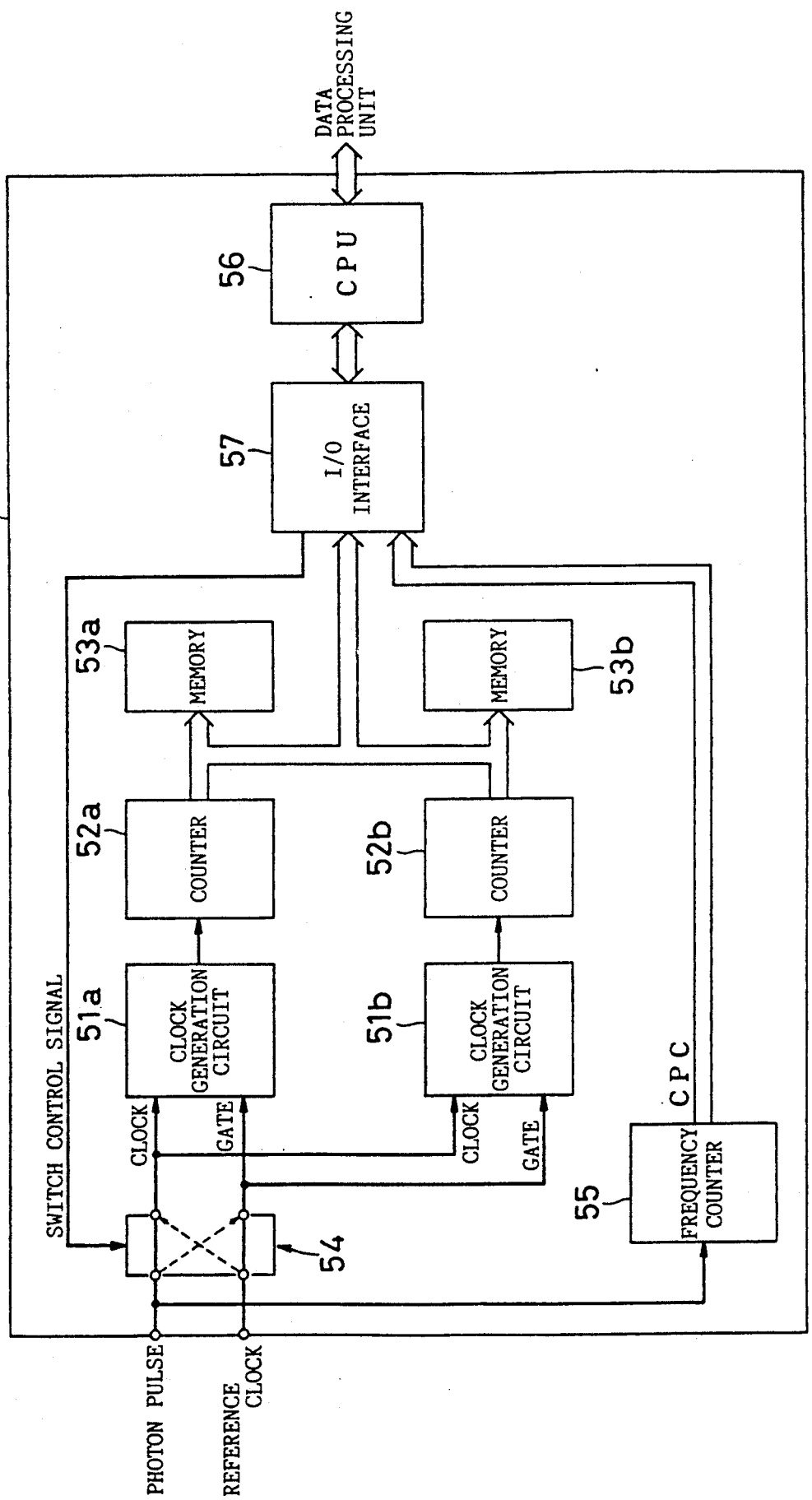
FIG. 2 is a block diagram of an example of a data measuring unit of the particle size measuring system of the present invention.

FIG. 2 is a block diagram of an example of the data generation unit 50. The data generation unit 50 includes: a pair of clock generation circuits 51a, 51b; counters 52a, 52b for respectively counting clocks supplied from the clock generation circuits 51a, 51b; memories 53a, 53b for respectively storing count data supplied from the counters 52a, 52b; a switch circuit 54 for selectively supplying a photon pulse and a reference clock to clock input terminals and gate input terminals of the clock generation circuits 51a, 51b, respectively, or the reference clock and the photon pulse thereto, respectively; a frequency counter 55 for receiving a photon pulse; and an I/O interface 57 interposed between a CPU 56 and the memories 53a, 53b, the frequency counter 55 & the switch circuit 54.

More specifically, the clock generation circuits 51a, 51b are adapted to generate clock signals according to input signals supplied to the clock input terminals while signals are supplied to the gate input terminals. The clock generation circuits 51a, 51b are so arranged as to be selectively operated in an alternate manner. When photon pulses are entered, the frequency counter 55 is adapted to count the per-unit-time number of photon pulses to generate count data according to the frequency. The switch circuit 54 is controlled to be switched based on the fact that a control signal is supplied from the CPU 56 through the I/O interface 57. The switch circuit 54 is adapted to supply photon pulses to one input terminal out of the clock input terminals and the gate input terminals of the clock generation circuits 51a, 51b, and to supply reference clocks to the other input terminals thereof.

The data generation unit 50 having the arrangement above-mentioned, may be operated as outlined below.

When a changeover control signal supplied from the CPU 56 represents that the time domain method is to be selected, the switch circuit 54 is switched such that the photon pulses are supplied to the clock input terminals of the clock generation circuits 51a, 51b and the reference clocks are supplied to the gate input terminals thereof. On the contrary, when the changeover control signal represents that the time interval method is to be selected, the switch circuit 54 is switched such that the reference clocks are supplied to the clock input terminals of the clock generation circuits 51a, 51b and the photon pulses are supplied to the gate input terminals thereof.

Figure 5:
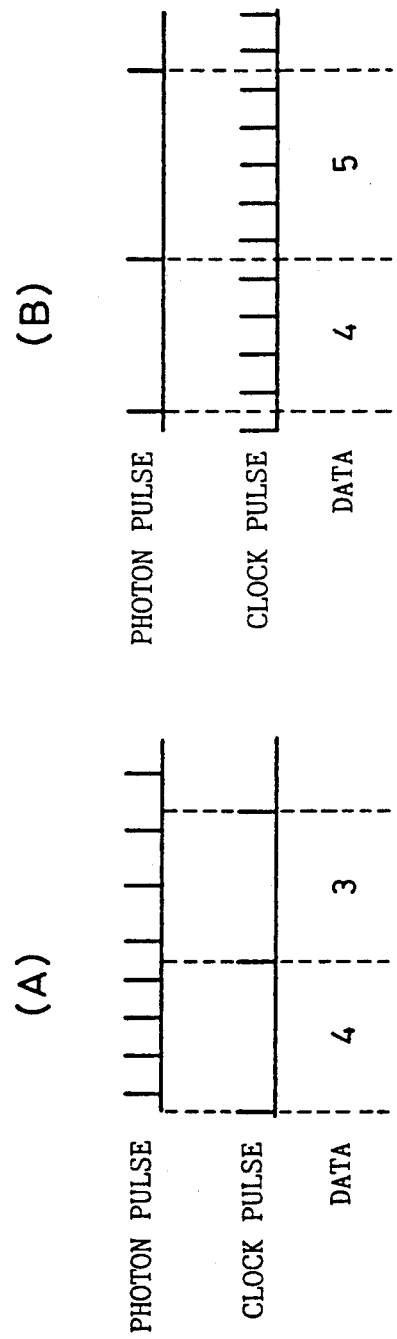
FIG. 5 (A) is a view illustrating how data are fetched according to the time domain method, while FIG. 5 (B) is a view illustrating how data are fetched according to the time interval method.

Accordingly, when the time domain method is selected, there are generated clocks of which number corresponds to the number of photon pulses within a period of time determined by the reference clocks, as shown in FIG. 5 (A). When the time interval method is selected, there are generated clocks of which number corresponds to the number of reference clocks within a photon pulse time interval, as shown in FIG. 5 (B).

The clocks generated selectively by the clock generation circuits 51a, 51b, are respectively counted by the counters 52a, 52b. The counted values are respectively stored in the memories 53a, 53b. As the result, the memories 53a, 53b alternately contain data forming time series data.

Thereafter, the data stored in the memories 53a, 53b may be alternately read out to form a chain of time series data, and the data processing unit 1 may execute necessary operations to calculate the particle size.

Figure 1:
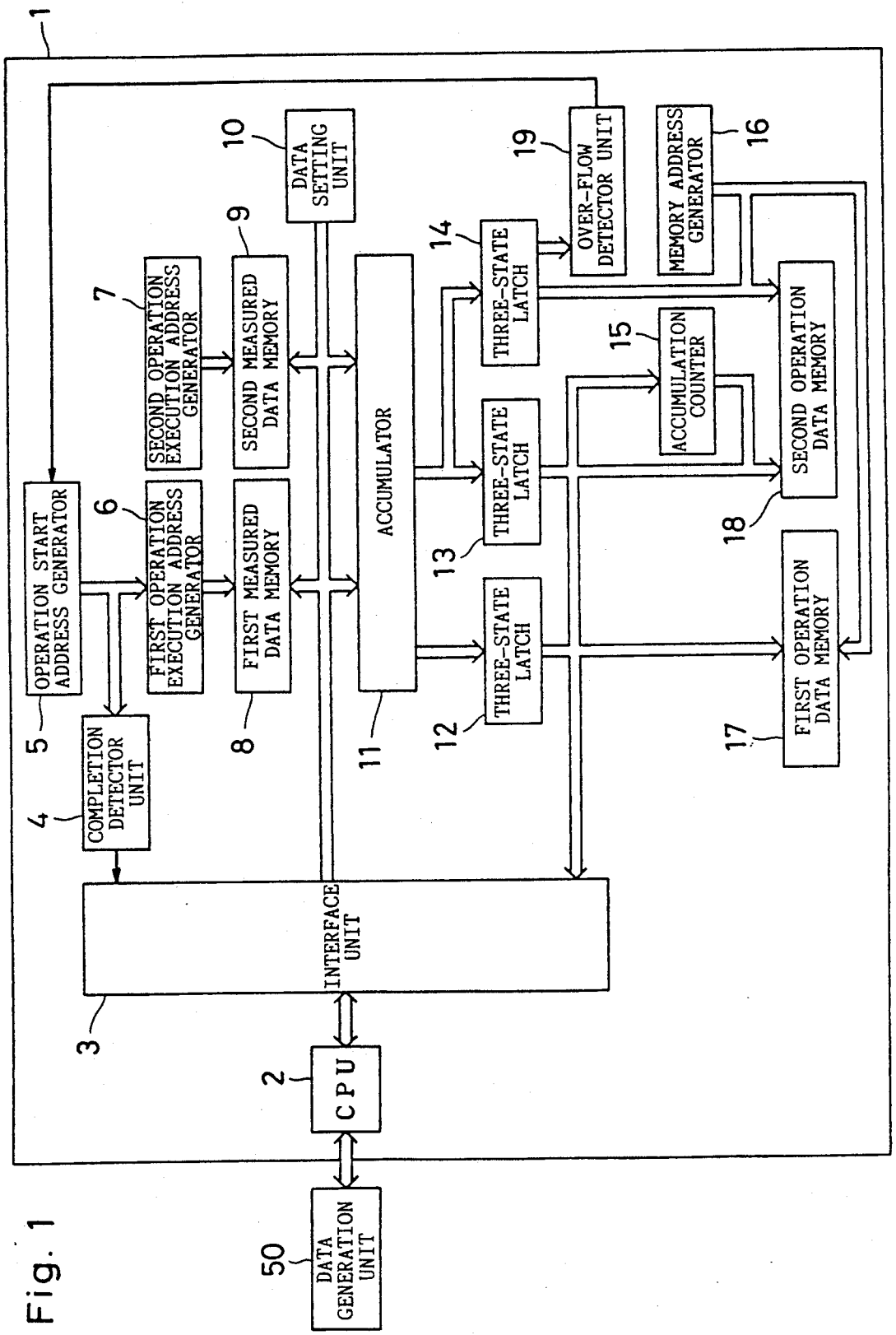
FIG. 1 is a block diagram of an example of a data processing unit of particle size measuring system in accordance with the present invention.

FIG. 1 is a block diagram of the data processing unit 1. The data generation unit 50 is connected at the output side thereof to an input port of a CPU 2. The output port of the CPU 2 is connected, through an interface unit 3, to first and second measured data memories 8, 9 for storing time series data, a completion detector unit 4 for detecting the completion of operations, and operation data memories 17, 18 for holding the operation results. There are also disposed first and second operation execution address generators 6, 7 for giving addresses for executing Σ operations to the measured data memories 8, 9, respectively. The first operation execution address generator 6 is connected to an operation start address generator 5. There are also disposed an accumulator 11 for receiving data from the measured data memories 8, 9 to execute multiplication and accumulation based on the data thus supplied. The operation result data from the accumulator 11 are latched by three-state latches 12, 13, 14, and supplied to the operation data memories 17, 18. There are also disposed an accumulation counter 15, a data setting unit 10, a memory address generator 16 and an over-flow detector unit 19.

Of the circuits above-mentioned, the second operation execution address generator 7, the measured data memory 9, the three-state latches 12, 13, the operation data memory 17 and the memory address generator 16 are used only for operations according to the time domain method. The data setting unit 10, the three-state latch 14, the accumulation counter 15 and the over-flow detector unit 19 are used only for operations according to the time interval method.

The circuits 1 to 19 may be composed of general purpose ICs. For example, the operation start address generator 5, the first operation execution address generator 6, the second operation execution address generator 7, the accumulation counter 15 and the memory address generator 16 may be formed by counters. The first measured data memory 8, the second measured data memory 9 may be formed by static RAMs. The accumulator 11 may be formed by a multiplier-accumulator. The three-state latches 12, 13, 14 may be formed by latch circuits. The operation data memories 17, 18 may be formed by static RAMs.

Thus, since the respective units are composed of independent ICs, the data processing unit may be made in a smaller size with less costs reduced to 1/10, as compared with a data processing unit using a mini-computer or the like.

The following description will discuss the steps for executing, in the data processing unit 1, an operation of $$\sum_{j=1}^{N-i} (n_{TDj} \times n_{TDj+i})$$

according to the time domain method.

To execute the operation expressed by the formula above-mentioned, it is required to calculate Σ for a range from $j=1$ to $j=N-i$ for each i ($i=1, 2, \ldots, M$).

Data representing the number of photon pulses $n_{TDj}$ measured by the data generation unit 50 are successively stored, through the CPU 2 and the interface unit 3, in the first and second measured data memories 8, 9.

Simultaneously, the operation start address generator 5 generates the address of a channel i (initially, i is set to 1, and thereafter, the following operation is repeatedly executed for $i=2, 3 \ldots$). The address thus generated is supplied to the first operation execution address generator 6. With the supplied address i serving as an initial value, the first operation execution address generator 6 supplies the address $j+1$ ($j=1, \ldots, N-i$) to the first measured data memory 8. On the other hand, the second operation execution address generator 7 supplies the address of j ($j=1, \ldots, N-i$) to the second measured data memory 9. The steps above-mentioned are repeatedly executed for $i=2, 3, \ldots, M$.

According to the supplied address data, the first and second measured data memories 8, 9 respectively supply already stored data representing the number of photon pulses $n_{TDj}$, $n_{TDj+i}$, to terminals a and b of the accumulator 11. The accumulator 11 executes an operation of $\Sigma(n_{TDj} \times n_{TDj+i})$ and respectively supplies the upper-digit output to the three-state latch circuit 12 and the lower-digit output to the three-state latch circuit 13.

The three-state circuits 12, 13 respectively supply these data to the first and second operation data memories 17, 18.

The operation data memories 17, 18 respectively write the data held by the three-state latch circuits 12, 13, in the memory area corresponding to the address i supplied from the memory address generator 16. This means that the operation data memories 17, 18 hold the data $\Sigma(n_{TDj} \times n_{TDj+1})$ at the area corresponding to the address i.

In the processing above-mentioned, there are simultaneously carried out (i) an operation for successively supplying addresses for $i=2, 3, \ldots M$ and $j=1, 2, N-i$ (in which N is a value as huge as, for example, 16,384) so that data are read from the first and second measured data memories 8, 9, and (ii) a multiplication & accumulation operation $\Sigma(n_{TDj} \times n_{TDj+i})$ by the accumulator 11. It is therefore expected to considerably reduce the operating period of time.

When the completion detector unit 4 detects that the address i generated by the operation start address generator 5 has exceeded the set number of channels M, the completion detector unit 4 supplies an operation completion signal to the CPU 2. Upon reception of the operation completion signal, the CPU 2 finishes the operation and reads data from the operation data memories 17, 18 to obtain the self correlation function as a function of i.

The following description will discuss the results of a test conducted according to the time domain method.

As a simulated photon pulse signal, a pulse signal having a pulse width of 40 nsec. and a pulse interval of 16 μsec was formed and sampled with a clock pulse signal having a pulse cycle of 20 μsec. With the RAM capacity set to 16 kbits (N=16,384) and the number of channels M varying, the measuring periods of time were obtained. The results are shown in Table 1. In the test, there was also used, as a conventional system, a system using a CPU 80286, 8MHz manufactured by INTEL Co., Ltd. and a coprocessor 80287, 8 MHz manufactured by INTEL Co., Ltd.

TABLE 1

| M | Present System | Conventional System |
| --- | --- | --- |
| 1024 | 6.0 sec. | 84.6 sec. |
| 512 | 3.2 | 43.2 |
| 256 | 1.9 | 22.0 |
| 128 | 1.2 | 11.2 |
| 64 | 0.8 | 5.8 |

As apparent from Table 1, the present system achieves a considerable reduction in measuring period of time. The following description will discuss the steps for calculating $$\sum_{j=s}^{p} n_{TIj} \ (p = s, s+1, s+2, \ldots)$$

to obtain the correlation data T(i), in the data processing unit 1 according to the time interval method.

To execute the operation expressed by the above formula, s is first set to 1. With p set to 1, $n_{TI1}$ is obtained. Then, with p set to 2, $\Sigma$ is calculated for a range from $j=1$ to $j=2$ (that is, $(n_{TI1}+n_{TI2}+n_{TI3}$ is obtained). Thereafter, the same operations are repeated for $p=4, 5, 6 \ldots$ When $$\sum_{j=s}^{p} n_{TIj}$$

reaches the maximum number of channels M or when p reaches N, the operations are finished. Then, the same operations are made for $s=2, 3, \ldots, N$.

First of all, the data $n_{TIj}$ representing the number of clock pulses measured in the data generation unit 50 are successively stored in the first measured data memory 8 through the CPU 2 and the interface unit 3.

Simultaneously, the operation start address generator 5 generates the address for s (initially, s is equal to 1), which is then supplied to the first operation execution address generator 6. With the address p=s serving as an initial value, the first operation execution address generator 6 supplies the address of j (j=s) to the first measured data memory 8. Subsequent to the operations above-mentioned, with p set to (s+1), the first operation execution address generator 6 supplies a series of addresses j (j=s, s+1) to the first measured data memory 8. Thereafter, a series of addresses j (j=s, s+1, s+2, ... p) are supplied to the first measured data memory 8 with the address p incremented.

According to a series of addresses thus supplied, the first measured data memory 8 reads and supplies already stored data representing the number of clock pulses $n_{TIj}$, to the terminal a of the accumulator 11. At this time, "1" is always supplied to the terminal b of the accumulator 11 by the data setting unit 10. Upon reception of both data, the accumulator 11 executes an operation of $$\sum_{j=s}^{p} (n_{TIj} \times 1)$$

and supplies the operation result to the three-state latch 14.

The three-state latch 14 supplies the data $$\sum_{j=s}^{p} n_{TIj},$$

as the address i, to the operation data memory 18. According to the address i thus supplied, the operation data memory 18 supplies the correlation data T(i) to the accumulation counter 15 each time the operation data memory 18 receives $$\sum_{j=s}^{p} n_{TIj} \text{ satisfying } i = \sum_{j=s}^{p} n_{TIj}.$$

It is noted that the first correlation data T(i) is equal to zero. The accumulation counter 15 adds "1" to the correlation data T(i) and returns the added data back to the operation data memory 18. Thus, the correlation data T(i) accumulated with respect to the respective addresses i are held in the operation data memory 18.

When the over-flow detector unit 19 detects that $$\sum_{j=s}^{p} n_{TIj}$$

entered to the three-state latch 14 has exceeded the preset number of channels M, the over-flow detector unit 19 supplies an instruction to the operation start address generator unit 5 to increment s by "1". Then, the first operation execution address generator 6 brings the increment of p to an end. Thereafter, the same operations are repeated for s=2, 3, ..., N.

In the processing above-mentioned, there are simultaneously carried out (i) an operation for successively supplying a series of address data from the first operation execution address generator 6 so that data are read from the measured data memories 8, 9, (ii) an accumulation operation for accumulating data in the accumulator 11, and (iii) an operation for counting the correlation data T(i) in the operation data memory 18 and the accumulation counter 15. It is therefore expected to considerably shorten the operating period of time.

Finally, when the correlation data T(i) accumulated in the operation data memory 18 are read, the CPU 2 calculates the self correlation function.

The following description will discuss the result of a test conducted according to the time interval method.

As a simulated photon pulse signal, a pulse signal having a pulse width of 40 nsec. and a pulse interval of 1.6 $\mu$sec was formed and a clock pulse signal having a pulse cycle of 0.8 $\mu$sec was used. Accordingly, $n_{Tij}$ is equal to 2. With the RAM capacity set to 16 kbits (N=16,384) and the number of channels M varying, the measuring periods of time were obtained. The results are shown in Table 2. In the test, there was also used, conventional system, a system using a CPU 80286, 8MHz manufactured by INTEL Co., Ltd. and a coprocessor 80287, 8MHz manufactured by INTEL Co., Ltd.

TABLE 2

| M | Present System | Conventional System |
|---|---|---|
| 1024 | 3.7 sec. | 62.8 sec. |
| 512 | 2.1 | 31.9 |
| 256 | 1.35 | 16.3 |
| 128 | 0.9 | 8.5 |
| 64 | 0.7 | 4.5 |

As apparent from Table 2, the present system applied to the time interval method also achieved a considerable reduction in measuring period of time.

As thus described, the present invention achieves reduction in measuring period of time. This enables the increase of the number of particle size measurements within a limited measuring period of time.

Figure 4:
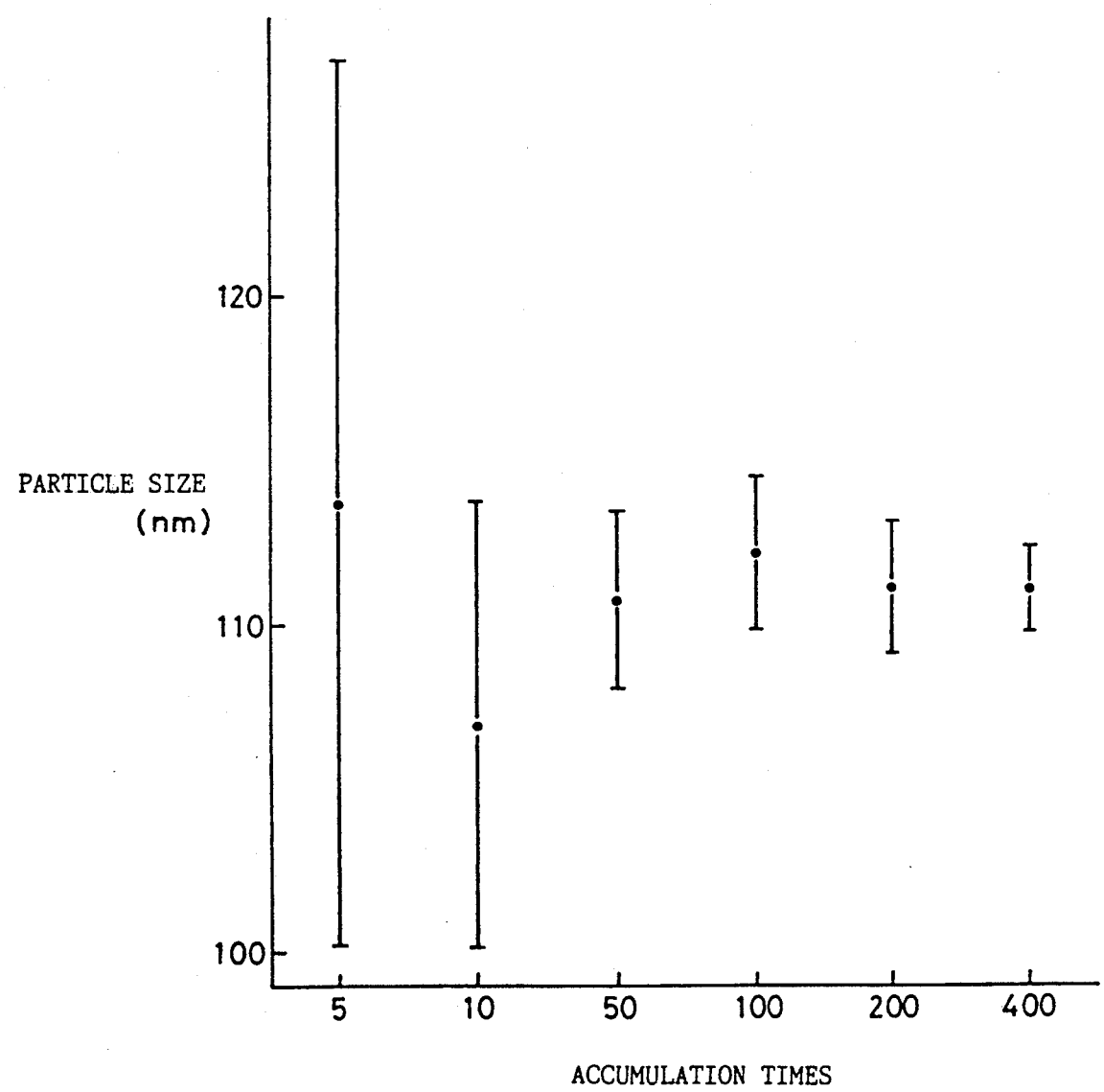
FIG. 4 is a view illustrating the measurement error distribution obtained for a standard latex.

FIG. 4 shows the error calculation distribution of a test in which there were used a 1000-times diluted solution containing, as a sample, a standard latex having a particle size of 109 nm, and a 10-$\mu$sec pulse signal as a reference clock, and in which the number of measurement channels was set to 256. In FIG. 4, black points represent the average particle sizes and the vertical rods represent particle size errors (standard deviations). It is apparent from FIG. 4 that the particle size errors are reduced with increase in the number of measurements It is a matter of course that the present invention should not be limited to the embodiment above-mentioned. In the embodiment above-mentioned, the present invention has been applied to a particle size measuring system of the type which automatically selects either the time domain method or the time interval method according to the scattering light intensity. The present invention is not limited to such an application. Of course, the present invention may be applied to a particle size measuring system for carrying out the time domain method or the time interval method alone.

While the present invention has thus been described with reference to the attached drawings, it will be obvious that the invention should not be limited to the particular embodiment above-mentioned, but the same may be varied in many ways without departing from the scope of the present invention.

We claim:

1. A particle size measuring system in which a laser light is irradiated to an object to be measured, time series data are generated based on the scattering light from the object to be measured, predetermined operations are executed based on the time series data thus generated, and the operation results are read and processed to obtain data representing the particle size of particles contained in the object to be measured, comprising:

time series data generating means for generating time series data representing the number of photon pulses per unit time;

first and second memories for storing said time series data;

reading means for successively reading, from said memories, time series data separated by a predetermined period of time from one another; and multiplication and accumulation operation means for multiplying the read time series data by one another, and for accumulating the multiplication results, the multiplication and accumulation being executed simultaneously with the reading operation by said reading means.

2. A particle size measuring system in which a laser light is irradiated to an object to be measured, time series data are generated based on the scattering light from the object to be measured, predetermined operations are executed based on the time series data thus generated, and the operation results are read and processed to obtain data representing the particle size of particles contained in the object to be measured, comprising:

time series data generating means for generating time series data representing a photon pulse time interval;

a memory for storing said time series data;

reading means for successively reading said time series data from said memory;

accumulation operation means for accumulating the read time series data over a predetermined range, the accumulation being simultaneously executed with the reading operation by said reading means;

a memory for successively storing the accumulation results; and counting means for reading, simultaneously with the accumulation operation by said accumulation operation means, the accumulation result data from said last-mentioned memory, thereby to obtain correlation data based on the number of said accumulation result data.

3. A particle size measuring system in which a laser light is irradiated to an object to be measured, time series data are generated based on the scattering light from the object to be measured, predetermined operations are executed based on the time series data thus generated, and the operation results are read and processed to obtain data representing the particle size of particles contained in the object to be measured, comprising:

(a) a first system including:

time series data generating means for generating time series data representing the number of photon pulses per unit time;

first and second memories for storing said time series data;

reading means for successively reading, from said memories, time series data separated by a predetermined period of time from one another; and multiplication and accumulation operation means for multiplying the read time series data by one another, and for accumulating the multiplication results, the multiplication and accumulation being executed simultaneously with the reading operation by said reading means, (b) a second system including:

time series data generating means for generating time series data representing a photon pulse time interval;

a memory for storing said time series data;

reading means for successively reading said time series data from said memory;

accumulation operation means for accumulating the read time series data over a predetermined range, the accumulation being simultaneously executed with the reading operation by said reading means;

a memory for successively storing the accumulation results; and counting means for reading, simultaneously with the accumulation operation by said accumulation operation means the accumulation result data from said last-mentioned memory, thereby to obtain correlation data based on the number of said accumulation result data, and (c) selection means for selecting, based on the intensity of scattering light, the time series data generating means of said first system, or the time series data generating means of said second system.

* * * * *